(12) United States Patent
Winge

(10) Patent No.: US 6,518,406 B1
(45) Date of Patent: Feb. 11, 2003

(54) METHOD FOR PURIFICATION OF PROTEINS

(75) Inventor: Stefan Winge, Årsta (SE)

(73) Assignee: Octapharma AG, Lachen (CH)

( * ) Notice: Subject to any disclaimer, the term of this patent is extended or adjusted under 35 U.S.C. 154(b) by 0 days.

(21) Appl. No.: 09/598,883

(22) Filed: Jun. 21, 2000

Related U.S. Application Data

(60) Provisional application No. 60/141,950, filed on Jul. 1, 1999.

(30) Foreign Application Priority Data

Jun. 23, 1999 (SE) ............................................. 9902388

(51) Int. Cl.$^7$ ............................. C07K 1/14; C07K 1/30; C07K 14/435
(52) U.S. Cl. ....................... 530/393; 530/412; 530/418; 530/419
(58) Field of Search ................................. 530/383, 412, 530/415, 418, 419, 359, 393

(56) References Cited

U.S. PATENT DOCUMENTS

| | | | |
|---|---|---|---|
| 4,340,589 A | 7/1982 | Uemura et al. | 424/101 |
| 4,977,246 A | 12/1990 | Lee et al. | 530/383 |

FOREIGN PATENT DOCUMENTS

| | | |
|---|---|---|
| JP | 9659506 | 3/1996 |
| WO | WO9426287 | 11/1994 |

OTHER PUBLICATIONS

WPI Derwent's Abstract No. 1996–263789 of Japanese Reference No. 81–9140, Apr. 30, 1996.*
Mitra et al, BioTechnology and Bioengineering, vol. XXIV; pp. 97–107, 1982.*
The Merck Index, 12th ed. Editor–Budavari, Merck & Co. Inc. Whitehouse Station, N.J. Entry Nos. 7722 and 7742, 1996.*
WPI Derwent's Abstract No. 1996–263789 of Japanese Reference No. 81–9140 dated Apr. 30, 1996.
Wickerhauser et al, *Vox Sanguinis*, 36:281–293 (1979).
Mitra et al, *Biotechnology and Bioengineering*, vol. XXIV:97–107 (1982).
Einarsson et al, *Transfusion*, 29(2):148–152 (1989).
Tengborn et al, *Thrombosis Research*, 48:701–711 (1987).

* cited by examiner

*Primary Examiner*—Christopher S. F. Low
*Assistant Examiner*—Anish Gupta
(74) *Attorney, Agent, or Firm*—Sterne, Kessler, Goldstein & Fox P.L.L.C.

(57) ABSTRACT

The present invention relates to methods for purification of antithrombin-III (AT-III) by precipitation of impurities. The said methods comprise (a) adding, to a solution comprising antithrombin-III, a saccharide and citrate, in an amount sufficient for impurities to precipitate while antithrombin-III essentially remains in solution; (b) allowing impurities to precipitate; and (c) removing the precipitated impurities, thereby obtaining a solution comprising purified antithrombin-III. The invention also relates to pharmaceutical compositions, obtainable by the said methods, comprising purified antithrombin-III, as well as to reconstituted pharmaceutical compositions essentially free from visible particles.

11 Claims, No Drawings

METHOD FOR PURIFICATION OF PROTEINS

CROSS-REFERENCE TO RELATED APPLICATIONS

The present application claims benefit to the filing date of U.S. Provisional Application Ser. No. 60/141,950, filed Jul. 1, 1999, and to Sweden 9902388-9, filed Jun. 23, 1999.

TECHNICAL FIELD

The present invention relates to methods for purification of antithrombin-III (AT-III) by precipitation of impurities. The invention also relates to pharmaceutical compositions obtainable by the said methods.

BACKGROUND ART

Antithrombin III (AT-III) is a plasma glycoprotein that inhibits serine proteases in the coagulation cascade and thus plays a major role in the regulation of blood clotting. A small decrease of the AT-III content in the blood is associated with increased risk of thromboembolism. AT-III concentrates are used in the prophylaxis and treatment of thromboembolic disorders in patients with acquired or hereditary antithrombin deficiency.

Generally, AT-III is isolated from human plasma and administered to the bloodstream of the patient. Consequently, virus inactivation of AT-III concentrates is desirable. Precipitation with polyethylene glycol (PEG) has been widely used in AT-III purification for concentrating the protein and for precipitating viruses (see e.g. Wickerhauser et al. (1979) Vox Sanguinis 36, 281). In addition to PEG, also barium sulfate, ethanol, trichloroacetic acid, dextran- and ammonium sulfate have been used as precipitating agents during purification of AT-III. Many of these precipitating agents would be harmful if present in the final AT-III formulation. Consequently, subsequent removal of these agents is necessary, and the recovery of AT-III is thereby reduced.

PEG precipitation alone is not sufficient to ensure complete removal of hepatitis virus. AT-III concentrates for therapeutical use are therefore normally pasteurized, normally at +60° C. for 10 h. In general, plasma proteins lose activity during heat treatment. For this reason, stabilizing agents are used during pasteurization.

Citrate and carbohydrates, such as sucrose, have been used as stabilizing agents for AT-III during pasteurization (Mitra et al. (1982) Biotechnology and Bioengineering vol. XXIV, 97–107; Tengborn et al. (1987) Thrombosis Research 48, 701–711; Einarsson et al. (1989) Transfusion 29, 148–152). However, there is no indication in these documents that citrate and saccharides can be used as precipitation agents in the purification of AT-III.

As a final step in the purification of AT-III, the formulation is often lyophilized. Many attempts have been made to prolong the shelf life of lyophilized AT-III.

U.S. Pat. No. 4,340,589 (Uemura et al.) discloses a lyophilized preparation of AT-III, stabilized with at least one substance selected from amino acids, saccharides, polysaccharides, etc., more specifically albumin, urokinase, gelatin, mannitol, heparin, glycine and lysine.

Ashizawa et al. (Japanese Patent Application No. 1994-199566) discloses lyophilized preparations of modified AT-III stabilized with one or more elements selected from organic acid salts, saccharides, amino acids and sodium chloride. The said organic salts could be sodium succinate or sodium citrate. The said saccharides could be D-mannitol, lactose, glucose and D-sorbitol. There is no indication in this document of lyophilized AT-III preparations comprising citrate in combination with sucrose.

A more or less known problem with liquid pharmaceutical preparations, is the formation of particles (approximately 2–75 um) after filling the product in vials or after reconstitution of freeze-dried products with a solution. Especially when working with larger molecules, like proteins, this is a phenomenon which relatively often occurs and the mechanism behind this is not clearly understood. Probably it is a combination of factors which affects in which amount and size the particles occurs, including molecular size of product, excepients of product, material of product container and solution in which the product is reconstituted in. It has not been shown that it should be of any danger having this relatively small amounts of particles in the products. However, it is obviously, that every pharmaceutical producer is aiming to reduce the amount of particles as much as possible in the products, especially the visible particles.

DISCLOSURE OF THE INVENTION

It has surprisingly been found that a combination of a saccharide, such as sucrose, and citrate can advantageously be used for precipitating impurities, including viruses and proteins other than AT-III, in the purification of AT-III. This procedure involves several advantages:

The precipitation step according to the invention assures high viral inactivation, high purity and minimal AT-III deactivation.

The obtained AT-III solution can be subjected directly to pasteurization without further addition of stabilizing compounds. Thus the combination of citrate and saccharide serves the dual purposes as precipitating agents and stabilizing agents during pasteurization.

There is no need to remove the pharmaceutically acceptable combination of saccharide and citrate during further purification of AT-III. Instead the precipitating agents are also useful as stabilizers of a lyophilized preparation of AT-III.

Consequently, in a first aspect this invention provides a process for purifying antithrombin-III comprising the steps of:

(a) adding, to a solution comprising antithrombin-III, a saccharide and citrate, in an amount sufficient for impurities in the said solution to precipitate while antithrombin-III essentially remains in solution;

(b) allowing impurities to precipitate; and (c) removing the precipitated impurities, thereby obtaining a solution comprising purified antithrombin-III.

In the present context, the term "impurities" is intended to mean undesired substances, including substances used during purification of AT-III (cf. Example 1, below). Impurities include e.g. histidine-rich glycoproteins, hemopexine, lipoproteins, gammaglobulins, Triton-X-100, tri-n-butyl-phosphate, virus, and prions.

The AT-III for use in the process according to the invention can be obtained by any suitable process and be of mammalian, e.g. bovine, porcine or, preferably, human origin. The AT-III may also be obtained by genetic engineering, such as by recombinant DNA techniques or from transgenic animals, e.g. from the milk of sheep producing AT-III in its milk.

Irrespective of origin, the AT-III can be of any isoform, e.g. α-AT-III or β-AT-III, or any derivative of AT-III. The difference between α-AT-III or β-AT-III is described e.g. by Brennan et al. (FEBS Letters 219(2), 431–436, 1987). The term "derivative of AT-III" refers e.g. to polypeptides carrying modifications like substitutions, small deletions, insertions or inversions, which polypeptides nevertheless have substantially the biological activities of AT-III.

The said saccharide is preferably a disaccharide such as sucrose or trehalose, or a monosaccharide such as glucose, sorbitol, mannitol, glyconic acid, or maltose. Sucrose is preferred because of its advantageous bioavailability in the body.

For precipitation of impurities, the concentration of saccharide can range from about 10% (w/v) to about 30% (w/v). Preferably the saccharide concentration is from between 15% and 25% (w/v), most preferably from about 20% (w/v).

The source of citrate can be citric acid or a pharmaceutically acceptable salt thereof, e.g. alkali metal citrates and alkaline earth metal citrates. Examples of alkali metal citrates are sodium and potassium citrate, while examples of alkaline earth metal citrates are magnesium and calcium citrate. For reasons of bioavailability, low cost and easy handling, sodium citrate is preferred.

For precipitation of impurities, the concentration of citrate can range from about 0.1 to about 3 M. Preferably the citrate concentration is from between 0.5 and 1.5 M, most preferably from between 1 M and 1.25 M.

During precipitation of impurities, pH can range from about 6 to about 9. Preferably, pH is from between 7 and 8, and most preferably neutral (around 7.5). The precipitation is suitably performed at a temperature from between +10° C. and +40° C., preferably at room temperature, such as from between +15° C. and +25° C.

Preferably, citrate and saccharide are added continuously to the solution under stirring during approximately 30 minutes. This procedure gives rise to a concentration gradient of saccharide and citrate. Since impurities might have a tendency to precipitate at different concentrations of the precipitating agents, such a gradient will optimize precipitation of impurities. A slow addition of the precipitating agents will also minimize the risk for high local concentrations of citrate and saccharide and thereby the risk for precipitation of AT-III.

In large-scale production, the solution is suitably stirred for approximately another 15 minutes after the final concentrations of saccharide and citrate have been reached.

The precipitated impurities are removed, suitably by filtration or centrifugation of the solution. A typical filtration step will comprise prefiltration trough a 1–20 $\mu$m filter, followed by sterile filtration through a 0.2 $\mu$m filter. If the choice is centrifugation, the skilled person will be able to determine suitable conditions with the aid of an ordinary textbook on protein purification. The filtrate or supernatant liquid comprising the antithrombin-III is then recovered in a form suitable for further processing.

In a further aspect, the invention comprises a process for purification of AT-III, wherein the precipitation step as described above is followed by pasteurization of the obtained solution comprising purified antithrombin-III, in the presence of a saccharide, in particular sucrose, and citrate as stabilizing agents. In a particularly preferred form of the invention, the already added amounts of saccharide and citrate will be sufficient as stabilizing agents during pasteurization, and consequently no further stabilizing agents will have to be added.

In yet a further aspect, the invention comprises a process for purification of AT-III as described above, in addition comprising lyophilization of antithrombin-III in the presence of a saccharide, in particular sucrose, and citrate as stabilizers. The same agents as previously used for precipitation and stabilization during pasteurization can conveniently be used also as stabilizers during lyophilization.

It will be understood by the skilled person that additional purification steps, subsequent to the pasteurization step, may be desirable to obtain AT-III in a form suitable for use or for lyophilization. Such steps can e.g. include, in any desired order:

Affinity chromatography, on a suitable medium such as Heparin-Sepharose®, in order to remove inactivated AT-III;
Ultrafiltration in order to concentrate and desalt AT-III;
Filtration for further removal of virus.

The skilled person will be able to perform necessary further purification steps by methods well known in the art. An example of AT-III purification is given in Example 1, below.

In another aspect, this invention provides a pharmaceutical composition obtainable by the methods as described above. The composition according to the present invention may be used as a liquid preparation without further processing. However, prior to administration the liquid preparation is suitably further processed by drying AT-III in the presence of stabilizers. A suitable method for drying is lyophilization. Other possible methods for drying include e.g. vacuum concentration.

Consequently, in a preferred form of the invention, the composition is a lyophilized AT-III composition having increased stability (prolonged shelf-life) compared with known AT-III compositions. The said composition comprises (i) antithrombin-III; and (ii) sucrose and citrate as stabilizing agents. It will be understood by the skilled person that the composition could optionally comprise additional pharmaceutically acceptable excipients and/or carriers, such as salts, e.g. sodium chloride; amino acids, e.g. lysine, alanine, glycine or histidine; surfactants, e.g. polysorbate 80, also known under the trademark Tween-80®; and other excipients such as polyethylene glycol (PEG 4000) or gluconic acid.

For preparation of a lyophilized AT-III composition according to the invention, a desired amount of the stabilizers is dissolved or preferably diafiltrated into an aqueous solution of AT-III having an appropriate concentration (from 50 to 1000 IU/ml, or from 5 to 200 mg/ml). The pH of the solution should be adjusted to from between 6 and 9, preferably from between 7 and 8. The solution is then sterile filtered, filled in vials, such as tubular glass bottles, and lyophilized.

The relative amount of sucrose in the composition is preferably from 0.5 to 2.5, more preferably from 1.0 to 1.5, parts per part antithrombin-III, by weight. The relative amount of citrate, preferably sodium citrate, is preferably from 1 to 4, more preferably from 2.5 to 3.0, parts per part antithrombin-III, by weight.

The AT-III composition according to the invention is further characterized in that it is stable without the addition of plasma-derived proteins, such as albumin. The absence of additional plasma-derived proteins increases the purity and viral safety in the composition of the invention.

When the pharmaceutical composition according to the invention is used to treat patients suffering from thromboembolic disorders, the lyophilized preparation can be dissolved in a physiologically isotonic salt solution or in sterile water, e.g. to a concentration of from 0.5 to 20% (w/v) of AT-III. The solution can be administered intravenously to obtain a systemic effect. It is, however, also possible to administer the solution to obtain a local effect, e.g. during balloon surgery of the coronary arteries.

As mentioned above, a more or less known problem with liquid pharmaceutical preparations, is the formation of visible particles (approximately 2–75 um) occurring after filling the product in vials, and particularly after reconstitution of freeze-dried products. Thus, a further aim of the present invention is to obtain a reconstituted products essentially free from such visible particles.

The inventor of the present application has surprisingly now found that adding a non-ionic surfactant to the reconstituted product in an amount of from at least 0.01% (w/w), provides a reconstituted AT-III product being essentially free from visible and undesired particles for a time period of as long as up to 3 months. The non-ionic surfactant is preferably selected from block co-polymers such as poloxamers, or polyoxyethylene sorbitan fatty acid esters, preferably polysorbate 80 (polyoxyethylene 20 sorbitan monooleate) which is also known under the trademark Tween 80®, as the reconstitution media. Any type of polyoxyethylene sorbitan fatty acid ester may be used as reconstitution media in accordance with the present invention, as long as it is pharmaceutically and pharmacologically acceptable. Further examples of such polyoxyethylene sorbitan fatty acid esters suitable for use in accordance with the present invention are polysorbate 20 (polyoxyethylene 20 sorbitan monolaurate), also known under the trademark Tween 20®; polysorbate 21 (polyoxyethylene(4)sorbitan monolaurate, also known under the trademark Tween 21®; polysorbate 40 (polyoxyethylene 20 sorbitan monopalmitate), also known under the trademark Tween 40®; polysorbate 60 (polyoxyethylene 20 sorbitan monostearate), also known under the trademark Tween 60®; polysorbate 61 (polyoxyethylene (4) sorbitan monostearate), also known under the trademark Tween 61®; polysorbate 65 (polyoxyethylene 20 sorbitan tristearate), also known under the trademark Tween 65®; polysorbate 81 (polyoxyethylene (5) sorbitan monooleate), also known under the trademark Tween 81®; polysorbate 85 (polyoxyethylene 20 sorbitan trioleate), also known under the trademark Tween 85®; and polysorbate 120 (polyoxyethylene 20 sorbitan monoisostearate), also known under the trademark Crillet 6®. Such polyoxyethylene sorbitan fatty acid esters are disclosed in *Handbook of pharmaceutical excipients*, 3$^{rd}$ edition, pp. 416–419, edited by Arthur H Kibble, which is hereby incorporated as reference.

Still another type of suitable surfactants useful in accordance with the present invention are sorbitan fatty acid esters. Any type of sorbitan fatty acid esters may be used as reconstitution media in accordance with the present invention, as long as it is pharmaceutically and pharmacologically acceptable. Suitable sorbitan fatty acid esters useful as reconstitution media in accordance with the present invention are disclosed in *Handbook of pharmaceutical excipients*, 3$^{rd}$ edition, pp. 511–514, edited by Arthur H Kibble, which is hereby incorporated in full as reference.

Experimental Methods

Biologic activity (IU/ml) of AT-III was determined as heparin cofactor activity by monitoring the cleavage of the chromogenic substrate H-D-Phe-Pip-Arg-pNA.2 HCl (Chromogenix, Sweden) by thrombin in presence of heparin and AT-III. See Frantzen Handeland et al. (Scand. J. Haematol. 31, 427–436, 1983) and van Voorhuizen et al. (Thromb. Haemostas. 52(3), 350–353, 1984).

Total protein concentration was determined by absorption measurements at 280 nm ($A_{280}$). Concentration (mg/ml) for AT-III solutions was calculated using the extinction coefficient of 6.4 IU/mg AT-III.

Specific activity of AT-III was defined as the ratio between heparin cofactor activity calculated as IU/ml and $A_{280}$.

Dimer and polymer content of AT-III was determined by high performance liquid chromatography (HPLC) gel filtration on a TSK G 3000 SW column (Toyosoda) with 10 $\mu$M particles and a pre-column (Toyosoda).

The amount of contaminating proteins was determined by crossed immuno-electrophoresis against anti-total human serum using standard conditions.

In order to determine that the reconstituted liquid pharmaceutical product is essentially free from visible particles, a sample is passing a detector, in which a laser source is transmitting light and a photosensor detects whenever a particle passes. The principle is called "light block principle". The amplified impulse from the photosensor is collected by the particle counter (Hiac Royco) and thereafter converted to particle size and amount.

EXAMPLES

Example 1

Preparation of Lyophilized AT-III from Human Plasma

Step 1. Precipitation of plasma. Human plasma is cryo-precipitated and centrifugate 1 is obtained by precipitating the resulting eluate with 8% ethanol at pH 7.2 and recovering the eluate as described by Cohn et al. (*J. Am. Chem. Soc.*, 72, 465, 1950).

Step 2. Affinity chromatography. Centrifugate 1 is processed through Heparin-Sepharose® (HS) gel equilibrated with 0.001 M $Na_2PO_3$, 0.15 M NaCl, at neutral pH. The HS gel binds approximately 10–15 IU AT-III per ml. The gel is washed with 0.4 M NaCl, 0.01M $Na_2PO_3$, pH 7.8 and AT-III is then eluted with 2 M NaCl, 0.01 M $Na_2PO_3$, pH 7.8.

Step 3. Ultra-filtration. The AT-III eluate is concentrated and desalted by ultra-filtration with 0.05 M $Na_2PO_3$, pH 7.5.

Step 4. S/D treatment. The AT-III filtrate is virus-inactivated by treatment with 1% (w/w) Triton X-100 and 0.3% (w/w) tri-n-butyl-phosphate (TNBP) according to the solvent/detergent (S/D) technology developed by New York Blood Center (see European patent application No. EP-A-0239859). The solvent and detergent are partly removed by extraction with 5% (w/w) soybean oil.

Step 5. Precipitation. A precipitation buffer containing 40% sucrose, 2.2 M sodium citrate, 0.05 M $Na_2PO_3$, pH 7.5 is added at room temperature to the solution, continuously during 30 minutes, to a final concentration of 20% (w/v) sucrose and 1.1 M sodium citrate. The solution is stirred for another 15 minutes and the precipitate is removed by decantation and the collected supernatant is filtered with following filters connected in series: 20–2 $\mu$m (Pall) ±0.45/0.22 $\mu$m (Sartorius). This step is intended to remove viruses; unwanted proteins; and remaining solvent and detergent compounds (cf. WO 94/26287).

Step 6. Pasteurization. To inactivate viruses the AT-III preparation is pasteurized for 10 hours at 60° C. Pasteurization is performed under nitrogen gas pressure and continuous stirring. During the pasteurization 20% (w/v) sucrose and 1.1 M sodium citrate act to stabilize AT-III against thermal inactivation.

Step 7. Affinity chromatography. The filtrate is diluted 1/11 with water. The affinity chromatography on Heparin-Sepharose is repeated to separate AT-III that was inactivated during the pasteurization. Heparin-Sepharose chromatography is performed as described in step 2.

Step 8. Ultrafiltration. The AT-III eluate is concentrated and desalted by ultrafiltration with 0.12 M NaCl, 0.001 M $Na_2PO_3$, pH 7.4.

Step 9. Virus filtration. Virus filtration is performed by adding NaCl to a concentration of 1 M in the AT-III solution before filtering through Viresolve™/70 (Millipore), using "dead end" technique as described in WO 96/00237.

Step 10. Ultrafiltration and lyophilization. The purified solution is concentrated and desalted by ultra filtration with 0.22 mol/kg sodium citrate, 0.07 mol/kg sucrose, 1.5 mmol/kg citric acid, pH 7.0, filled in vials and lyophilized. The obtained freeze-dried composition contains 2.8 mg sodium citrate and 1.3 mg sucrose per mg AT-III.

The total recovery of AT-III from plasma is approximately 60%. More than 95% of the protein content of the resulting lyophilized AT-III concentrate is AT-III. Furthermore, the AT-III protein present contains more than 95% of active AT-III, i.e. less than 5% of inactivated AT-III. The AT-III concentrate is furthermore virus-safe due to steps 4, 6 and 9, which are directed to removing and/or inactivating viruses. In addition, steps 1, 2, 5 and 7 bring about some degree of inactivation or removal of viruses.

Example 2
Virus Inactivation in the Precipitation Step

The virus removing effect of the precipitation step was determined by a virus study. The study was carried out on parvovirus, which is of the most difficult viruses to eliminate due to its small size (20–25 nm).

A solution of AT-III was contaminated with parvovirus and the precipitation step according to Example 1, Step 5, was conducted. The solution was analyzed with respect to parvovirus content before and after the precipitation step according to Example 1. The results indicated that the precipitation step reduces the content of parvovirus by at least a factor $10^2$.

Example 3
Purification and Yield in the Precipitation Step

A solution of AT-III containing impurities was divided into two aliquots. One was subjected to ion exchange chromatography (CM-Sepharose®, Amersham Pharmacia Biotech) and one to the precipitation step according to Example 1, step 5. Before and after the purification step, the aliquots were analyzed with respect to heparin cofactor activity and AT-III concentration. The results, shown in Table I, indicate that both methods had a purifying effect on the AT-III solution. The yield, determined as remaining heparin cofactor activity, was somewhat higher with the precipitation step.

TABLE I

| Sample | Specific Activity IU/(ml × $A_{280}$) | Yield (% IU) |
| --- | --- | --- |
| Starting material | 7 | 100 |
| After CM-gel | 11 | 85 |
| After precipitation | 11 | 90 |

Example 4
Effect of Various Precipitating Agents

The ability of various salts to precipitate impurities in an AT-III solution was determined. To an AT-III solution, obtained according to Example 1, step 4, various salts were added at neutral pH and at room temperature (+23° C.). The precipitate (if any) was removed and the specific activity of the supernatant solution was determined.

"Purification" was calculated using the protein concentration obtained with 1.25 M sodium citrate and 20% sucrose ("$A_{280\ inv}$") as a standard. The "Purification factor" was obtained by determining $A_{280}$ for each sample before and after addition of salt ("$A_{280ref}$" and "$A_{280sample}$", respectively) and using the formula $$A_{280ref(sample)} - A_{280sample} \times 100 / A_{280ref(inv)} - A_{280inv}.$$

Consequently, a purification factor zero indicates that there was no precipitation of impurities. The purification factors obtained with various salts are given in Table II.

Recovery was determined as per cent residual activity (% IU). The recovery was above 90% for all samples. The results thus indicate that an efficient purification and high recovery is obtained by using sodium citrate and sucrose.

TABLE II

| Precipitating agent | Purification factor |
| --- | --- |
| 1.25M sodium citrate and 20% sucrose | 100 |
| 1.25M sodium citrate | 75 |
| 1.25M sodium chloride | 0 |
| 2M sodium chloride | 0 |
| 4M sodium chloride | 0 |
| 1.25M sodium sulfate | 48 |
| 1.25M ammonium sulfate | 0 |
| 2M ammonium sulfate | 67 |
| 1.25M sodium acetate | 0 |
| 1.25M barium chloride | 0 |
| 1.25M potassium phosphate | 30 |

Example 5
Stability of Lyophilized AT-III

Various stabilizing agents were tested for effect on stability of AT-III during storage at +25° C. or +37° C., for 3 or 12 months. The results, shown in Tables III to VI, indicate that sodium citrate and sucrose in combination have advantageous effects on the stability of AT-III.

An advantageous combination of sodium citrate and sucrose, as stabilizers of lyophilized AT-III, is 2.8 parts of sodium citrate and 1.2 parts of sucrose, per part AT-III by weight.

TABLE III 3 months storage at +25° C.

| Stabilizer | mg stabilizer/IU AT-III | Residual activity (%) | Monomer (%) | Dimer (%) | Polymer (%) |
| --- | --- | --- | --- | --- | --- |
| albumin | 0.20 | 96 | 97.0 | 1.7 | 1.2 |
| glycine | 0.20 | 98 | 99.4 | 0.6 | 0.0 |
| lysine | 0.20 | 101 | 99.2 | 0.6 | 0.2 |
| citrate | 0.44 | 100 | 98.8 | 1.2 | 0.0 |
|  | 0.88 | 99 | 99.0 | 1.0 | 0.0 |
| sorbitol + citrate | 0.20 0.44 | 100 | 99.3 | 0.7 | 0.0 |
| trehalose + citrate | 0.20 0.44 | 100 | 99.2 | 0.8 | 0.0 |
| sucrose + citrate | 0.20 0.44 | 99 | 99.2 | 0.8 | 0.0 |

TABLE IV 3 months storage at +37° C.

| Stabilizer | mg stabilizer/IU AT-III | Residual activity (%) | Monomer (%) | Dimer (%) | Polymer (%) |
| --- | --- | --- | --- | --- | --- |
| alanine | 0.20 | 94 | 98.6 | 1.3 | 0.2 |
| albumin | 0.20 | 93 | 96.1 | 2.8 | 1.1 |
| glycine | 0.20 | 95 | 99.0 | 1.0 | 0.0 |
| lysine | 0.20 | 101 | 99.0 | 0.7 | 0.3 |
| citrate | 0.04 | 93 | 98.0 | 1.3 | 0.7 |
|  | 0.44 | 99 | 98.6 | 1.4 | 0.0 |

TABLE IV-continued

3 months storage at +37° C.

| Stabilizer | mg stabilizer/IU AT-III | Residual activity (%) | Monomer (%) | Dimer (%) | Polymer (%) |
|---|---|---|---|---|---|
|  | 0.88 | 98 | 99.2 | 0.8 | 0.0 |
| sorbitol + citrate | 0.20 0.44 | 100 | 99.2 | 0.8 | 0.0 |
| trehalose + citrate | 0.20 0.44 | 100 | 99.1 | 0.9 | 0.0 |
| sucrose + citrate | 0.20 0.44 | 99 | 99.2 | 0.8 | 0.0 |

TABLE V

12 months storage at +25° C.

| Stabilizer | mg stabilizer/IU AT-III | Residual activity (%) | Monomer (%) | Dimer (%) | Polymer (%) |
|---|---|---|---|---|---|
| albumin | 0.20 | 94 | 94.8 | 3.8 | 1.4 |
| glycine | 0.20 | 96 | 99.1 | 0.9 | 0.0 |
| lysine | 0.20 | 99 | 98.0 | 1.5 | 0.5 |
| citrate | 0.44 | 102 | 98.6 | 1.4 | 0.0 |
|  | 0.88 | 98 | 98.8 | 1.2 | 0.0 |
| sorbitol + citrate | 0.20 0.44 | 100 | 98.9 | 1.1 | 0.0 |
| trehalose + citrate | 0.20 0.44 | 100 | 98.7 | 1.3 | 0.0 |
| sucrose + citrate | 0.20 0.44 | 99 | 98.8 | 1.2 | 0.0 |

TABLE VI

12 months storage at +37° C.

| Stabilizer | mg stabilizer/IU AT-III | Residual activity (%) | Monomer (%) | Dimer (%) | Polymer (%) |
|---|---|---|---|---|---|
| albumin | 0.20 | 91 | 91.7 | 6.6 | 1.7 |
| glycine | 0.20 | 94 | 98.5 | 1.5 | 0.0 |
| lysine | 0.20 | 98 | 98.7 | 0.6 | 0.7 |
| citrate | 0.44 | 99 | 96.9 | 2.8 | 0.4 |
|  | 0.88 | 96 | 98.1 | 1.9 | 0.0 |
| sorbitol + citrate | 0.20 0.44 | 97 | 98.9 | 1.1 | 0.0 |
| trehalose + citrate | 0.20 0.44 | 100 | 98.8 | 1.2 | 0.0 |
| sucrose + citrate | 0.20 0.44 | 97 | 98.9 | 1.1 | 0.0 |

Example 6
Preparation of a Lyophilized Composition of AT-III 2.8% (w/v) sodium citrate and 1.2% (w/v) sucrose were added to 1% (w/v) aqueous solution of AT-III. pH was adjusted to 7.0 and the solution was sterile filtered (Millipore), filled in vials and lyophilized.

Example 7
Comparison Between a Formulation According to the Invention and an AT-III Formulation Comprising Albumin Antithrombin-III was purified according to Example 1. Two formulations were prepared as follows:

Formulation A

125 IU/ml antithrombin; 0.4 mg sodium citrate/IU antithrombin; 1 µg citric acid/IU antithrombin; 0.2 mg sucrose/IU antithrombin; pH 7.0.

Formulation B

125 IU/ml antithrombin; 0.2 mg sodium chloride/IU antithrombin; 0.2 mg albumin/IU antithrombin; 1 µg sodium phosphate/IU antithrombin; 4 µg acetyltryptophan/IU antithrombin; 3 µg sodium caprylate/IU antithrombin; pH 7.0.

Samples were sterile filtered and filled in tubular glass bottles under aseptic conditions and lyophilized. The bottles were sealed under vacuum and analyzed shortly thereafter.

The results, shown in Tables VII and VIII, indicate that Formulation A, according to the invention, had an advantageous effect on AT-III stability when compared with Formulation B.

TABLE VII

Formulation A

| Sample no. | IU/vial | Water residue % | Activity, % heparincofactor | Aggregation, % monomer | Specific activity, IU/mg protein |
|---|---|---|---|---|---|
| 1 | 500 | 4.4 | 92 | 99 | 6.5 |
| 2 | 500 | 4.3 | 99 | 99 | 7.0 |
| 3 | 500 | 3.1 | 98 | 99 | 6.6 |
| 4 | 1000 | 3.1 | 98 | 99 | 6.6 |
| 5 | 1500 | 4.9 | 97 | 99 | 6.8 |

TABLE VIII

Formulation B

| Sample no. | IU/vial | Water residue % | Activity, % heparincofactor | Aggregation, % monomer | Specific activity, IU/mg protein |
|---|---|---|---|---|---|
| 1 | 500 | 0.7 | n.d. | 97 | 3.1 |
| 2 | 500 | 0.7 | n.d. | 98 | 3.2 |
| 3 | 500 | 0.7 | n.d. | 97 | 3.0 |
| 4 | 1000 | 0.6 | n.d. | 98 | 3.1 |
| 5 | 1000 | 0.2 | 94 | n.d. | n.d. |
| 6 | 1000 | 0.2 | 96 | n.d. | n.d. |
| 7 | 1000 | 0.2 | 96 | n.d. | n.d. |
| 8 | 1500 | 0.3 | n.d. | 98 | 3.2 |
| 9 | 1500 | 0.1 | 94 | n.d. | n.d. |
| 10 | 1500 | 0.2 | 94 | n.d. | n.d. |
| 11 | 1500 | 0.2 | 94 | n.d. | n.d. |
| 12 | 1500 | 0.3 | 92 | n.d. | n.d. |
| 13 | 1500 | 0.2 | 98 | n.d. | n.d. | n.d. = not determined

Example 8
Comparison of Different Reconstitution Media's Ability of Inhibiting the Formation of Particles, After Reconstitution of AT-III Formulation A in Example 7, According to the Invention.

Freeze dried bottles of antithrombin(500 IU), according to formulation A of example 7, were reconstituted to 50 IU/ml with the following reconstitution media's (all media was sterile filtered (Millipore) before use):

a) Water for injection
b) 0.15M sodium chloride
c) 0.025M sodium phosphate pH 7.4
d) 0.01% polysorbate 80 (Tween 80®)
e) 0.15M lysine pH 7.4
f) 0.15M glycine
g) 0.15M alanin The bottles were able to stand in 22° C. for 24 hour and were then visually inspected regarding the formation of particles. The only reconstitution media in which no particles could be detected was 0.01% polysorbate 80 (Tween 80®), in all others there were a similar amount of particle generation.

Example 9

Comparison of Different Concentrations of Polysorbate 80 (Tween 80®) Ability of Inhibiting the Formation of Particles, After Reconstitution of AT-III Formulation A in Example 7, According to the Invention.

Freeze dried bottles of antithrombin(500 IU), according to formulation A of example 7, were reconstituted to 50 IU/ml with the following different concentration of polysorbate 80 (Tween 80®) (all media were sterile filtered (Millipore) before use):

a) 0.0100%(w/w) polysorbate 80 (Tween 80®)
b) 0.0050%(w/w) polysorbate 80 (Tween 80®)
c) 0.0010%(w/w) polysorbate 80 (Tween 80®)
d) 0.0001%(w/w) polysorbate 80 (Tween 80®)
e) Water for injection The bottles were able to stand in 22° C. and visually inspected regarding the formation of particles after 0 h, 2 h, 16 h, 42 h, 5 days, 11 days, 1 month, 2 months and 3 months

| Sample | 0 h | 2 h | 16 h | 42 h | 5 days | 11 days | 1 month | 2 months | 3 months |
|---|---|---|---|---|---|---|---|---|---|
| 0.01%   | − | −  | −   | −   | −   | −   | −   | −   | −   |
| 0.005%  | − | −  | −   | −   | −   | −   | +   | +   | +   |
| 0.001%  | − | +  | +   | +   | +   | +   | +++ | +++ | +++ |
| 0.0001% | − | ++ | +++ | +++ | +++ | +++ | +++ | +++ | +++ |
| 0%      | − | ++ | +++ | +++ | +++ | +++ | +++ | +++ | +++ |

− No particles could be detected
+ Some particles could be detected
++ Particles could be detected
+++ A lot of particles could be detected −No particles could be detected
+Some particles could be detected
++Particles could be detected
+++A lot of particles could be detected The only reconstitution media in which no particles could be detected after 3 months was 0.01% polysorbate 80 (Tween 80®), in all others, some or a lot of particles could be detected.

Example 10

Comparison of 0.01% Polysorbate 80

(Tween 80®) and water's ability of inhibiting the formation of particles, after reconstitution of AT-III formulation A in example 7, according to the invention.

Freeze dried bottles of antithrombin (500 IU), according to formulation A of example 7 were reconstituted to 50 IU/ml with 0.01% polysorbate 80 (Tween 80®) and water for injection (all media was sterile filtered (Millipore) before use). The bottles were stored in 22° C. for 24 h and then the particles were counted and size defined, using a particle counter (Hiac Royco):

| Particle size [μm] | Rec. with water, [particles/ml] | Rec. with 0.01% Tween 80 ®, [particles/ml] |
|---|---|---|
| 2  | 12013 | 1264 |
| 5  | 3956  | 253  |
| 10 | 1029  | 37   |
| 15 | 376   | 6    |
| 20 | 180   | 1    |
| 25 | 94    | 0    |
| 30 | 55    | 0    |
| 35 | 33    | 0    |
| 40 | 18    | 0    |
| 45 | 10    | 0    |
| 50 | 5     | 0    |
| 55 | 3     | 0    |
| 60 | 2     | 0    |
| 65 | 1     | 0    |
| 70 | 1     | 0    |
| 75 | 1     | 0    |

As shown in the table above, visual particles (above 20um), which is the main inhibitory object, is totally inhibited when the product, according to the invention, is reconstituted with 0.01%(w/w) polysorbate 80 (Tween 80®).

What is claimed is:

1. A process for purifying antithrombin-III, comprising the steps of:

(a) adding, to a solution comprising antithrombin-III, a saccharide and citrate, in an amount sufficient for impurities to precipitate while antithrombin-III essentially remains in solution;
   (b) allowing impurities to precipitate; and
   (c) removing the precipitated impurities, thereby obtaining a solution comprising purified antithrombin-III.

2. The process according to claim 1, wherein the saccharide is selected from the group consisting of monosaccharides and disaccharides.

3. The process according to claim 2, wherein the saccharide is a monosaccharide.

4. The process according to claim 1, wherein the concentration of saccharide is from 10 to 30%.

5. The process according to claim 4, wherein the concentration of saccharide is from 15 to 25%.

6. The process according to claim 1, wherein the saccharide is sucrose.

7. The process according to claim 1, wherein the concentration of citrate is from 0.1 to 3 M.

8. The process according to claim 7, wherein the concentration of citrate is from 0.5 to 1.5 M.

9. The process according to claim 1, wherein the source of citrate is sodium citrate.

10. The process according to claim 1, further comprising a pasteurization step of the obtained solution comprising purified antithrombin-III in the presence of the saccharide and citrate as stabilizing agents.

11. The process according to claim 1, further comprising a lyophilization step.

* * * * *